(12) United States Patent
Newman

(10) Patent No.: US 9,717,399 B2
(45) Date of Patent: Aug. 1, 2017

(54) ENDOSCOPE WITH MULTIFUNCTIONAL EXTENDIBLE ARMS AND ENDOSCOPIC INSTRUMENT WITH INTEGRATED IMAGE CAPTURE FOR USE THEREWITH

(71) Applicant: ENDOPODIUM, INC., Escondido, CA (US)

(72) Inventor: Allen Newman, Rancho Santa Fe, CA (US)

(73) Assignee: ENDOPODIUM, INC., Escondido, CA (US)

( * ) Notice: Subject to any disclaimer, the term of this patent is extended or adjusted under 35 U.S.C. 154(b) by 460 days.

(21) Appl. No.: 14/042,704

(22) Filed: Sep. 30, 2013

(65) Prior Publication Data

US 2014/0094655 A1    Apr. 3, 2014

Related U.S. Application Data

(60) Provisional application No. 61/707,844, filed on Sep. 28, 2012, provisional application No. 61/707,846, filed on Sep. 28, 2012.

(51) Int. Cl.
*A61B 1/00* (2006.01)
*A61B 1/04* (2006.01)
(Continued)

(52) U.S. Cl.
CPC ............ *A61B 1/05* (2013.01); *A61B 1/0008* (2013.01); *A61B 1/00174* (2013.01);
(Continued)

(58) Field of Classification Search
CPC ............ A61B 1/0008; A61B 1/00183; A61B 1/00181; A61B 2017/3482;
(Continued)

(56) References Cited

U.S. PATENT DOCUMENTS 5,279,575 A * 1/1994 Sugarbaker ........ A61B 17/3403
 604/104
5,857,999 A * 1/1999 Quick ................ A61B 17/3421
 604/104

(Continued)

*Primary Examiner* — John P Leubecker
*Assistant Examiner* — Aaron B Fairchild
(74) *Attorney, Agent, or Firm* — Scott H. Davison; Musick Davison LLP

(57) ABSTRACT

An endoscope and methods of use thereof are provided, which includes at least one multi-functional extending arm supporting a plurality of imaging, lighting and other sensory elements. The arms provide a mounting platform upon which cameras, lights and sensors may be mounted to generate multiple-angled images and video, arena-like lighting and other data for performing a minimally-invasive surgical (MIS) procedure. The arms may be inserted through a single portal in the endoscope and extended outward in multiple directions from the single portal once inserted into a body cavity. The endoscope may also include support arms which support the extending arms within the body cavity and a stabilization plate which anchors the endoscope to an external surface of the body. An endoscopic tool with optical, lighting and other sensors integrated into a functional end is also provided.

11 Claims, 10 Drawing Sheets

(51) Int. Cl.
*A61B 1/06* (2006.01)
*A61M 5/32* (2006.01)
*A61B 1/05* (2006.01)
A61B 17/34 (2006.01)
A61M 25/02 (2006.01)

(52) U.S. Cl.
CPC ...... *A61B 1/00181* (2013.01); *A61B 1/00183* (2013.01); *A61B 1/0676* (2013.01); *A61B 2017/3482* (2013.01); *A61B 2017/3484* (2013.01); *A61B 2017/3492* (2013.01); *A61M 2025/0233* (2013.01)

(58) Field of Classification Search
CPC .... A61B 2017/3484; A61B 2017/3492; A61B 17/1155; A61B 2017/3419; A61B 2017/348
USPC ........ 227/175.1; 600/146; 604/174; 606/108
See application file for complete search history.

(56) References Cited

U.S. PATENT DOCUMENTS

| | | | | |
|---|---|---|---|---|
| 6,066,090 A | * | 5/2000 | Yoon | A61B 1/00045 600/146 |
| 2009/0030276 A1 | * | 1/2009 | Saadat | A61B 1/00089 600/112 |
| 2011/0306832 A1 | * | 12/2011 | Bassan | A61B 1/00009 600/109 |

* cited by examiner

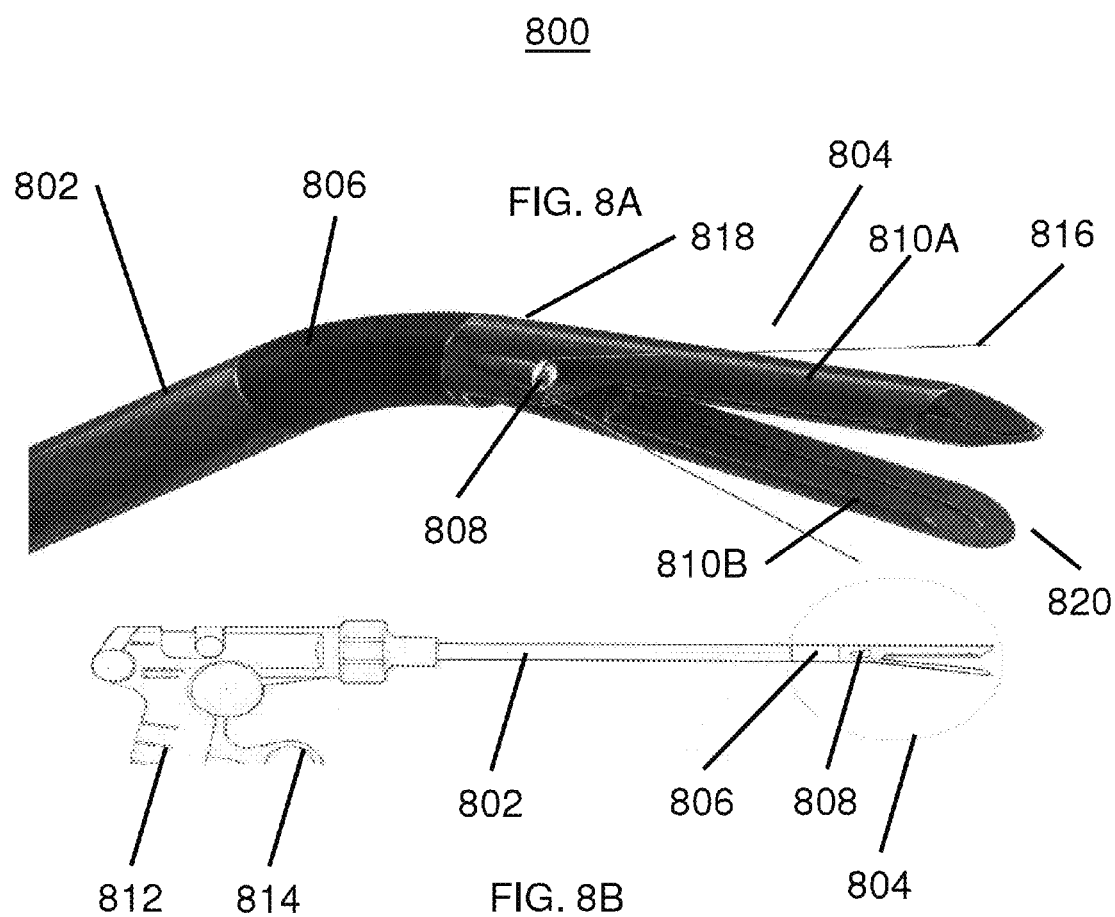

ENDOSCOPE WITH MULTIFUNCTIONAL EXTENDIBLE ARMS AND ENDOSCOPIC INSTRUMENT WITH INTEGRATED IMAGE CAPTURE FOR USE THEREWITH

BACKGROUND

1. Technical Field

The embodiments described herein are related to an endoscope with a plurality of multifunctional extending arms and an endoscopic tool with an integrated camera for use therewith, and more particularly to an endoscope with a plurality of extending, multi-functional arms upon which a plurality of cameras, lighting and other sensory elements may be mounted and which can be used in conjunction with the camera-mounted endoscopic tool.

2. Background

An endoscope is a medical optics device which is used to look inside the human body. It may include a tube known as a cannula which contains optical elements and a light source for capturing images on a distal end of the tube which are viewed by a user outside the body through a monitor or an eyepiece. The endoscope is commonly used for diagnostics and for performing minimally-invasive surgery (MIS), where only small openings are made in the dermis and body walls through which the endoscope is inserted. A user, such as a surgeon performing a medical procedure, will insert the endoscope through an opening in the body, after which the surgeon may insert a medical instrument through another opening with which they can perform the medical procedure while viewing it through the optics in the endoscope.

Endoscopes are limited by the optics implemented in the endoscope and the resulting ability to clearly view an area within the human body while performing a medical procedure. When the optical elements of the endoscope are inserted separately from the medical instrument, it is difficult to view the medical instrument and the work that is being done. Additionally, manipulating the medical instrument to perform the medical procedure and the endoscope to ensure proper viewing of the procedure is often exceedingly difficult, requiring careful manipulation and coordination to move both devices. In some situations, more than one medical instrument is inserted and must be manipulated simultaneously with the other inserted medical instruments all while continuously repositioning the endoscope for a proper view. Additionally, in cases where the medical instrument must move around an object within the body, such as an organ, tissue, bone, etc., the endoscope may be unable to follow the medical instrument and provide adequate images of an area of interest. The benefits of performing MIS are hampered by the lack of visual and other information available to the surgeon.

SUMMARY

Embodiments described herein provide an endoscope and methods of use thereof which includes at least one multi-functional extending arm supporting a plurality of imaging, lighting and other sensory elements. The multi-functional extending arms provide a mounting platform upon which cameras, lights and sensors may be mounted to generate multiple-angled images and video, arena-like lighting and other data relevant to performing a medical diagnostic or minimally-invasive surgical (MIS) procedure. The multi-functional extending arms may be inserted through a single portal in the endoscope and extended outward in multiple directions from the single portal once inserted into a body cavity. The endoscope may also include support arms which support the extending arms within the body cavity and a stabilization plate which anchors the endoscope to an external surface of the body. The extending arms may also include communication elements to transmit, either wired or wirelessly, the images and other data generated by the sensory elements to a remote computing and display device.

Embodiments described herein also provide a medical instrument with an integrated image capture device for use with an endoscope in minimally-invasive surgery (MIS). The image capture device may be mounted near an end portion of the medical instrument where the medical instrument interfaces with tissue so that images can be generated anywhere the medical instrument is directed without requiring manipulation and guidance of a separate endoscope. In one embodiment, the image capture device may be a CMOS camera that can easily be implemented on a medical instrument used for MIS. One or more lighting devices may also be implemented into an end portion of the medical instrument to provide sufficient illumination for the image capture device. In one embodiment, the medical instrument may be inserted into a body cavity through a cannula in the endoscope.

In one aspect of the invention, an endoscope with a multifunctional extending arm, comprises a central shaft with a distal end and a proximal end, and configured to be inserted through a cannula and into a body cavity; at least one extendible arm configured at the distal end of the central shaft, wherein the at least one extendible arm is configured to extend away from the central shaft when the distal end has protruded through the cannula and into the body cavity; wherein the at least one extendible arm is configured with at least one sensor element.

BRIEF DESCRIPTION OF THE DRAWINGS

The accompanying drawings, which are incorporated in and constitute a part of the specification, illustrate embodiments of the invention and, together with the description, serve to explain the objects, advantages, and principles of the invention. In the drawings:

FIG. 8A is a detailed perspective view of an endoscopic tool with an image capture device mounted at a base portion thereof, according to one embodiment of the invention; and FIG. 8B is a general side-view illustration of the endoscopic tool illustrating a handle and an operating trigger for remotely actuating the endoscopic tool at an end portion where the endoscopic tool interfaces with tissue, according to one embodiment of the invention.

DETAILED DESCRIPTION

After reading this description it will become apparent to one skilled in the art how to implement the invention in various alternative embodiments and alternative applications. However, all the various embodiments of the present invention will not be described herein. It is understood that the embodiments presented here are presented by way of an example only, and not limitation. As such, this detailed description of various alternative embodiments should not be construed to limit the scope or breadth of the present invention as set forth below.

Embodiments described herein provide an endoscope with a plurality of extending arms which can be inserted into a body cavity through a single entry point made by the endoscope and then extended outward from the single entry point to provide a plurality of imaging, lighting and sensory elements around an area inside the body cavity where a minimally-invasive surgery (MIS) is being performed. The extending arms may extend from the single entry point at a variety of angles in order to provide images and lighting from multiple angles, giving a person performing the MIS, such as a surgeon, significantly improved imagery of an area within the body cavity.

Embodiments described herein also provide a medical instrument with an integrated image capture device positioned at an interfacing end of the medical instrument where the medical instrument interfaces with tissue during a minimally-invasive surgical (MIS) procedure. The medical instrument may be any type of endoscopic tool used during MIS, such as scissors, graspers, dissectors, staplers, etc. The interfacing end of the medical instrument may then be the portion of the medical instrument where the actual scissor blades, grasper clamps, staple arms, etc. are located. In one embodiment, the image capture device may be integrated at a base section of the interfacing end so that a user can view the movement of the medical instrument as it performs its function.

I. Multi-Winged Endoscope

Figure 1:
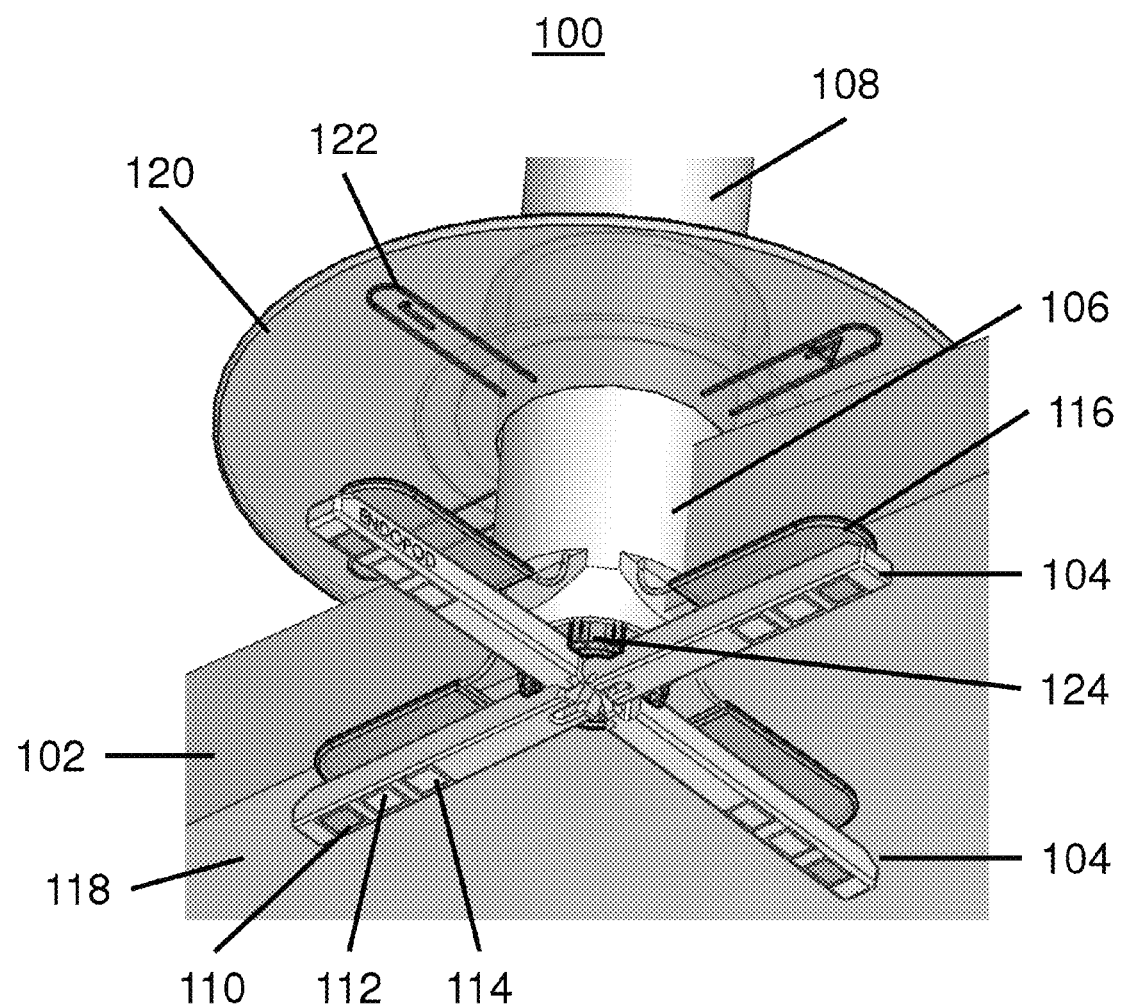
FIG. 1 is a perspective view illustration of an endoscope inserted into a body cavity as viewed from within the body cavity and in an extended configuration with a plurality of extendible arms configured with lighting elements, optical elements and sensor elements, support arms and a stabilization plate, according to one embodiment of the invention.

FIG. 1 is an illustration of one embodiment of the multi-winged endoscope 100 viewed from within a body cavity and showing the endoscope 100 inserted through an abdominal wall 102 of a body. A plurality of extending arms 104 are shown in an extended position such that they extend away from a central entry point 106 at 90 degree angles from each other. Although the descriptions and illustrations shown herein provide for four separate extendible arms, the endoscope may be configured with as few as one extendible arm and more than four. In one embodiment, in order to provide an optimal image, each of the arms 104 may also be zeroed out, meaning they lie along the same plane and have an angle differential of zero. The extending arms 104 may initially be folded up into a cannula 108, where they are then pushed into the body cavity and then extended and folded outward as the endoscope 100 is inserted into the body cavity. Each extending arm 104 may be configured with at least one optical element 110, such as a CMOS image sensor, which captures images and video from its unique perspective. The extending arms are also configured with a plurality of lighting elements 112, such as LEDs, which provide bright light, are inherently small so as to be easily implemented into the extending arms, and require minimal power while producing very little heat.

The extending arms 104 may also be configured with other sensor elements 114, such as temperature, audio or spatial sensors to provide a user with additional data from within the body cavity. In one embodiment, the sensor element 114 is a laser which projects onto a surface of the body cavity and is used to measure distance or to provide guidance for an endoscopic tool. Other sensors may be configured to detect near infrared (near IR), fluorescence from a dye (such as chromoendoscopy) and chemo and other visual cues, such as speed, electrical signals or movement of tissues and fluids. The extending arms may also include communication hardware and software used to transmit the images, videos and other sensor data from each extending arm to a display or computing device. The communication device may transmit the images and data through a wired connection through the central entry point or wirelessly to a nearby display device.

As shown in FIG. 1, the endoscope may also include a plurality of support arms 116 located adjacent to and primarily disposed above the extending arms 104 and which also extend outward from the central entry point 106. The support arms 116 are configured to rest against an interior surface 118 of the abdominal wall 102 to hold the endoscope in place. A stabilization plate 120 may be disposed surrounding the cannula 108 and positioned against an exterior surface (see FIG. 2B) of the abdominal wall 102 outside the body cavity. The stabilization plate 120 may act together with the support arms 116 to keep the endoscope locked in position against the abdominal wall 102. The stabilization plate may also function as a guide for determining the location of the extending arms and corresponding optical elements within the body cavity by providing a numerical arm guide 122 illustrating a silhouette of the extending arm along with a number corresponding to each extending arm so that the user can determine the location of each image being generated by the imaging device in the extending arm. In one embodiment, the stabilization plate 120 may be rotated about the axis of the cannula 108 and in conjunction with rotation of the extension arms 104 and the support arms 116 to provide different views of the body cavity. A set of tabs 124 may protrude from a distal end of the cannula between adjacent extendible arms 104 so that when the cannula 108 and stabilization plate 120 are rotated, the tabs 124 also rotate and cause the extendible arms to rotate at the same time.

In another embodiment, each individual extension arm 104 may detent, or be rotated along its length-wise axis to tilt the extension arm 104 to obtain a different view of the body cavity. The opposing extension arm 104 which extends in a parallel direction from the cannula may also be configured to rotate along with its opposing extension arm to provide a stereoscopic view of the body cavity from the same angle.

Figure 2A:
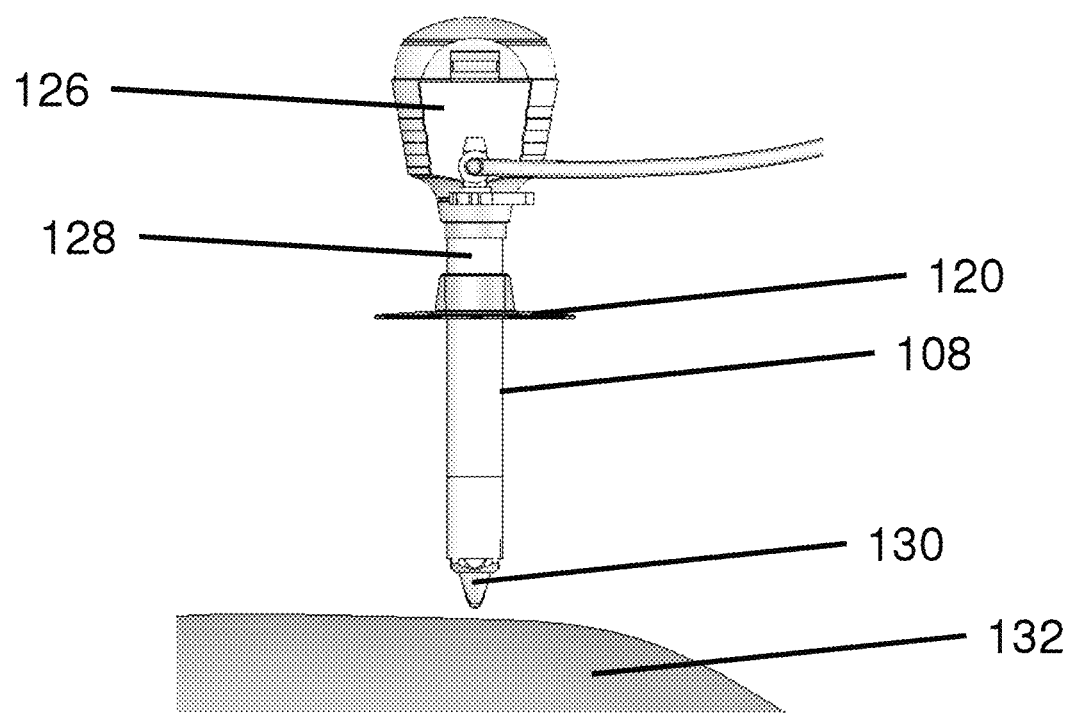
FIG. 2A is a side view illustration of an endoscope insertion housing showing a cannula, housing and trocar prior to insertion of the trocar through an abdominal wall and into the body cavity, according to one embodiment of the invention.
Figure 2B:
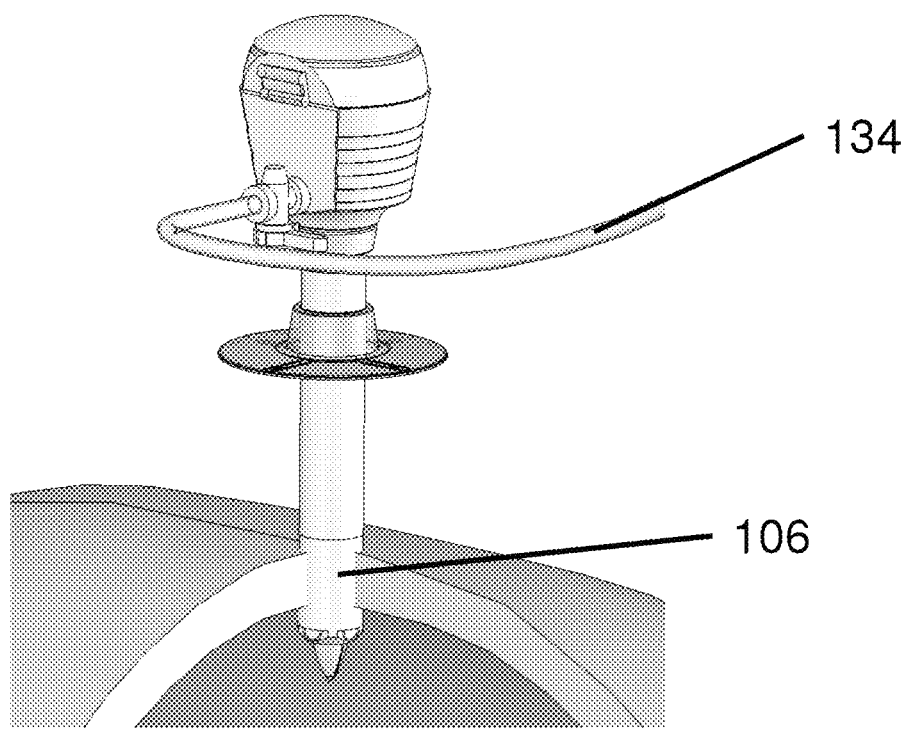
FIG. 2B is a perspective view illustration of the endoscope insertion housing upon insertion of the trocar through the abdominal wall and into the body cavity, according to one embodiment of the invention.

FIGS. 2A-2F illustrate a process of inserting the endoscope through an abdominal cavity and into a body cavity. FIG. 2A shows an endoscope insertion housing 126 in an initial configuration with a trocar 128 positioned within the cannula 108. The trocar 128 is disposed with a sharp point 130 or needle which is used to puncture the abdominal wall 102 to create the opening 106 in the exterior surface 132, as shown in FIG. 2B, after which the cannula 108 is inserted through the opening created by the trocar. A gas input tube 134 is connected with the insertion housing 126 in order to insert gas into the body cavity in order to distend the body cavity to make it easier to view during a surgical procedure.

Figures 2C, 2D:
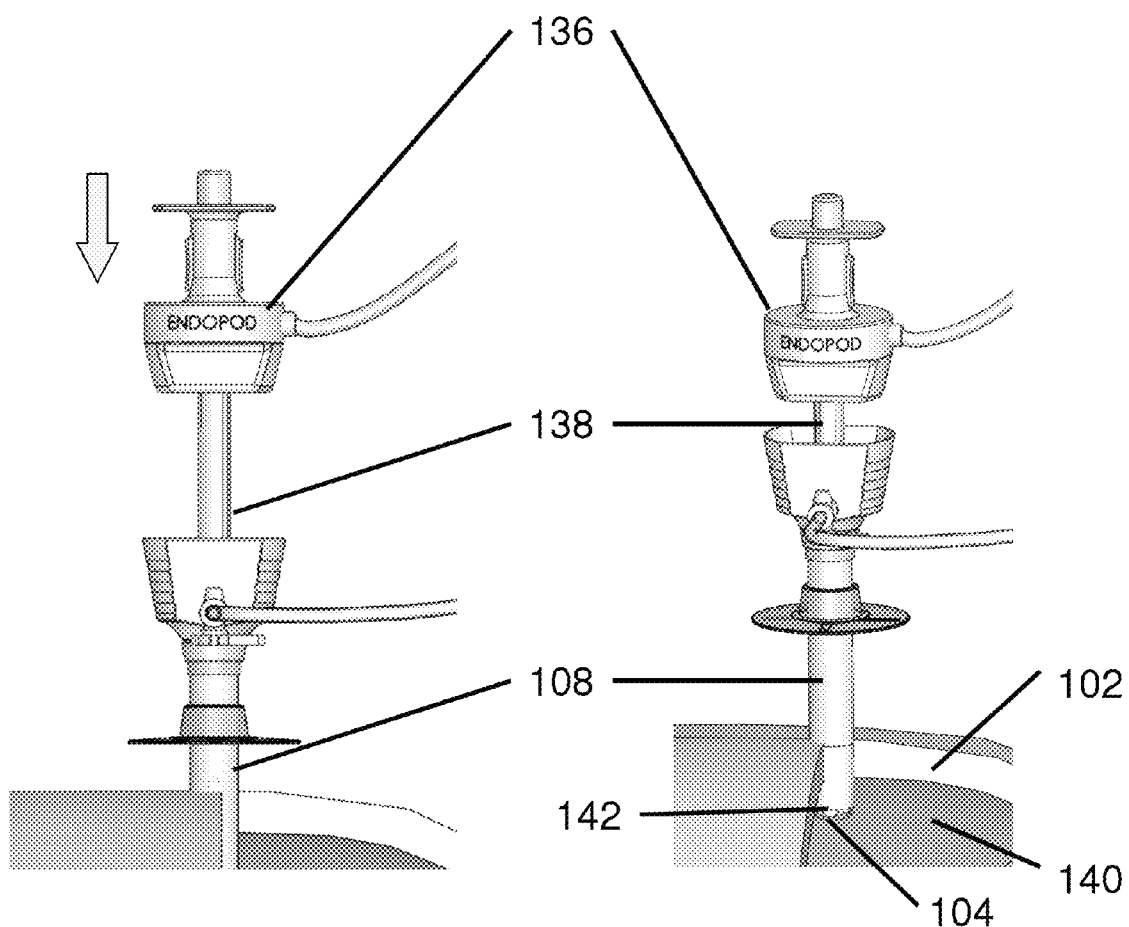
FIG. 2C is a side view illustration of the endoscope being inserted through the cannula and into the body cavity after the trocar is removed, according to one embodiment of the invention.
FIG. 2D is a perspective view illustration of the endoscope upon insertion through the cannula and into the body cavity, according to one embodiment of the invention.
Figures 2E, 2F:
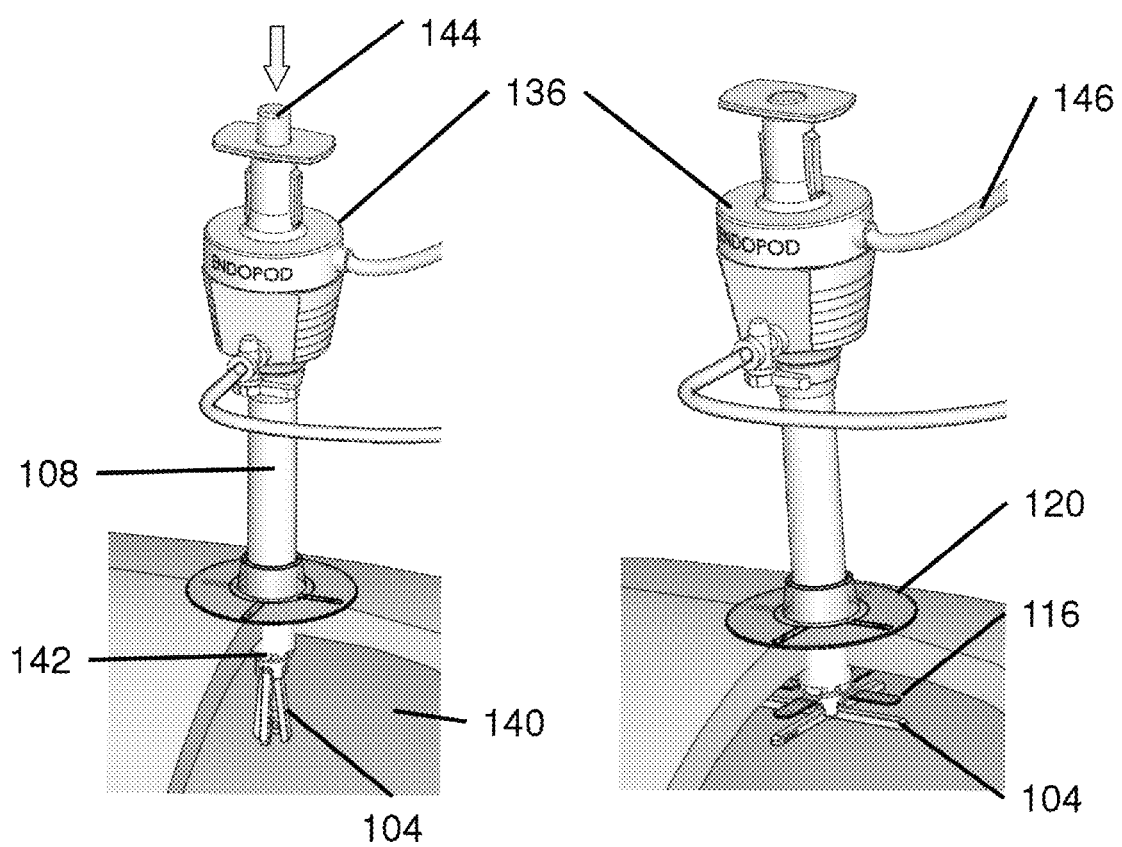
FIG. 2E is a perspective view illustration of the endoscope in a partially-extended configuration during activation of the extension button, according to one embodiment of the invention.
FIG. 2F is a perspective view illustration of the endoscope in an extended configuration with full extensions of the plurality of extending arms and support arms, according to one embodiment of the invention.

In FIGS. 2C and 2D, the trocar 128 has been removed and the multi-winged endoscope 136 is now positioned over the cannula 108, such that a central shaft 138 with the extendible arms disposed on a distal end thereof is inserted through the cannula 108 and into the body cavity 140. As shown in FIG. 2D, once the central shaft 138 has been passed substantially into the cannula 108, the extendible arms 104 on the distal end begin to protrude through a distal opening 142 of the cannula 108 within the body cavity. FIGS. 2E and 2F illustrate the expansion and extension of the extendible arms 104 via the actuation of an extension button 144 on a proximal end of the endoscope once the central shaft 138 is substantially disposed within the cannula 104 and the extendible arms 104 have protruded out of the distal opening 142 of the cannula 108 and into the body cavity 140. The extension button 144 may have a spring-actuated mechanism or a simple mechanical connection along the central shaft 138 with the extendible arms 104 and support arms 116 which causes the extendible arms 104 to protrude outward from the cannula 108. The support arms 116 and stabilization plate 120 are also illustrated in an extended configuration in FIG. 2F, with the extendible arms and support arms extended at perpendicular angles to the cannula and separated from each adjacent arm by a 90 degree (right) angle. The multi-winged endoscope is additionally provided with an optoelectronic cable 146 which transmits the electrical connections needed to power the optical elements, lighting elements and sensor elements, as well as transmitting the data collected by the optical elements and sensor elements to an computing device (not shown) for processing and displaying of the images and other collected data.

Figure 3:
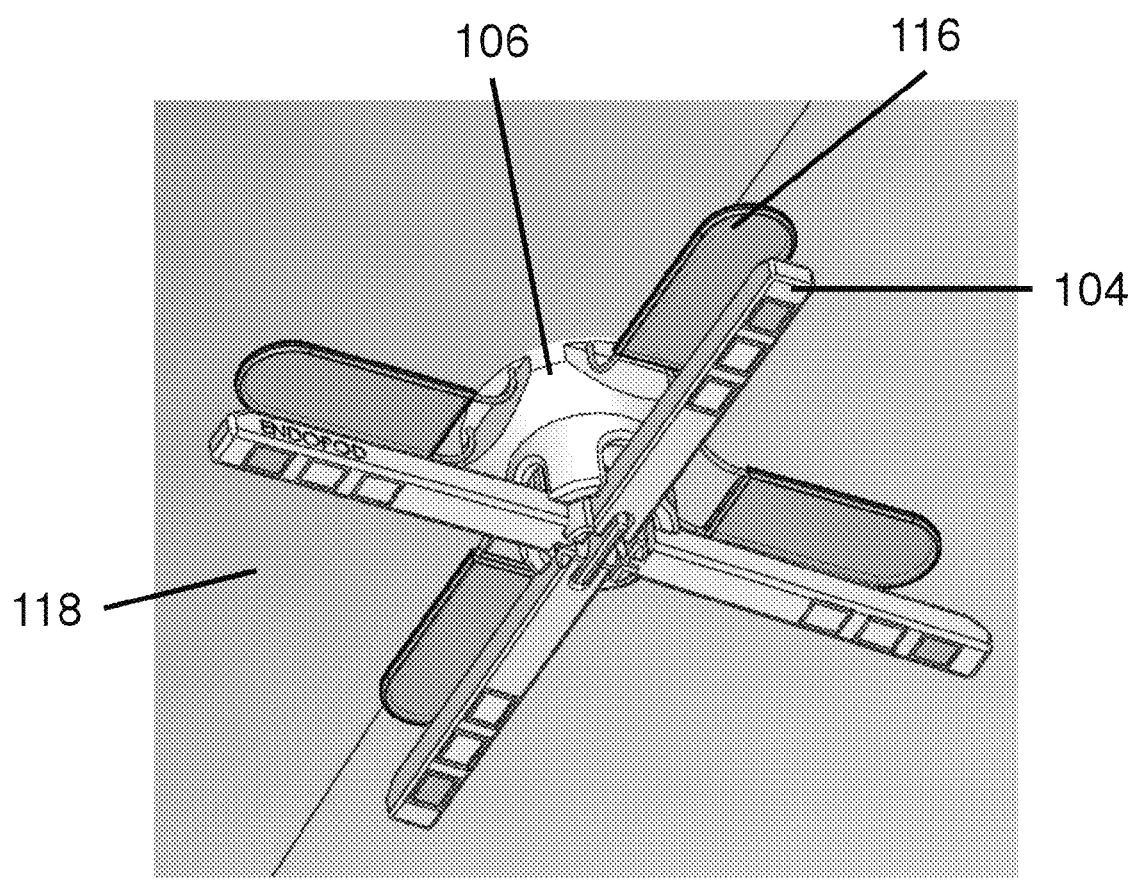
FIG. 3 is a perspective view illustration from within the body cavity of the support arms in contact with an inner abdominal wall, according to one embodiment of the invention.

FIG. 3 is a bottom perspective view of the plurality of extendible arms 104 and corresponding support arms 116 as inserted through the single opening 106 in the abdominal wall. FIG. 3 illustrates a locked position of the endoscope where the support arms 116 are in their extended configuration such that they are spaced away from the extendible arms 104 but in direct contact with the inner surface 118 of the abdominal wall 102 to help stabilize the endoscope.

In one embodiment, the support arms 116 are locked into position against the inner abdominal wall 118 in conjunction with positioning the stabilization plate 120 against the skin surface 132. The stabilization plate 120 may be connected with the support arms 116 via a detend.

Figure 4:
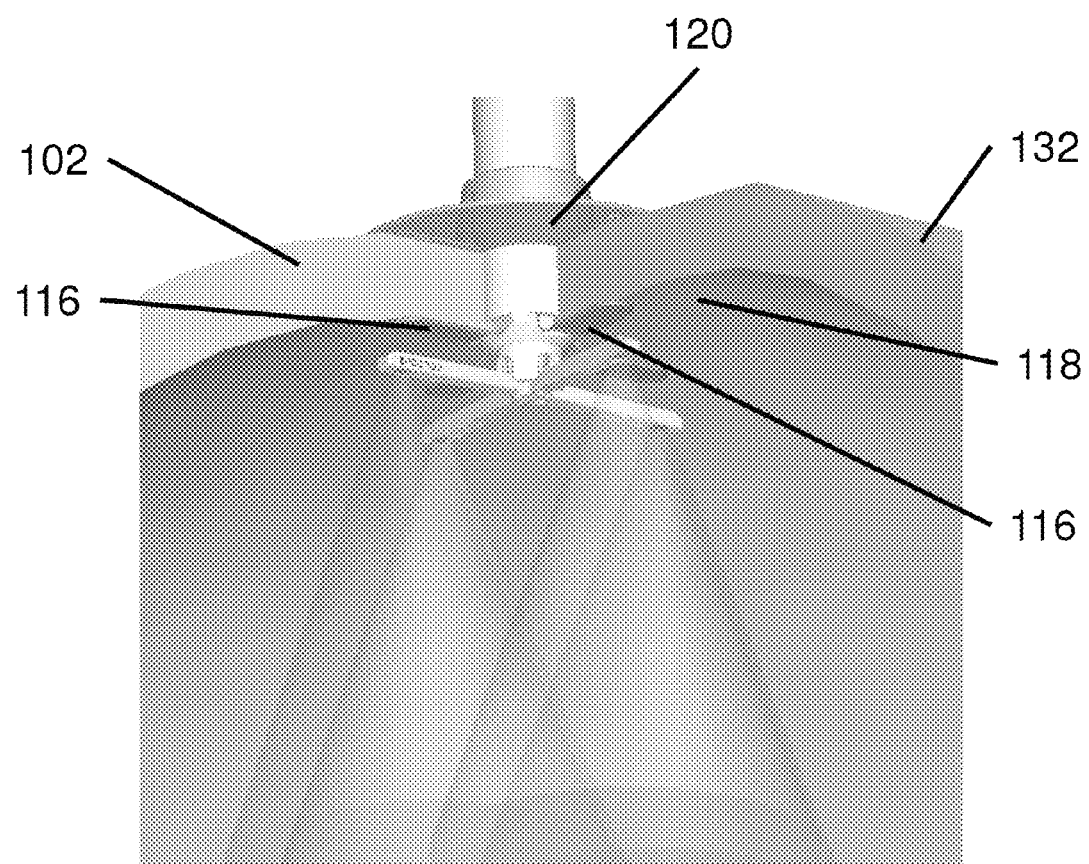
FIG. 4 is a side perspective cut-away view illustration of the endoscope in the extended configuration, according to one embodiment of the invention.

FIG. 4 illustrates a side perspective cut-away view of the endoscope in the locked position, which more clearly illustrates how the support arms 116 are in direct contact with the inner surface 118 of the abdominal wall 102 while the corresponding stabilization plate 120 is also flush against the skin surface.

Figure 5:
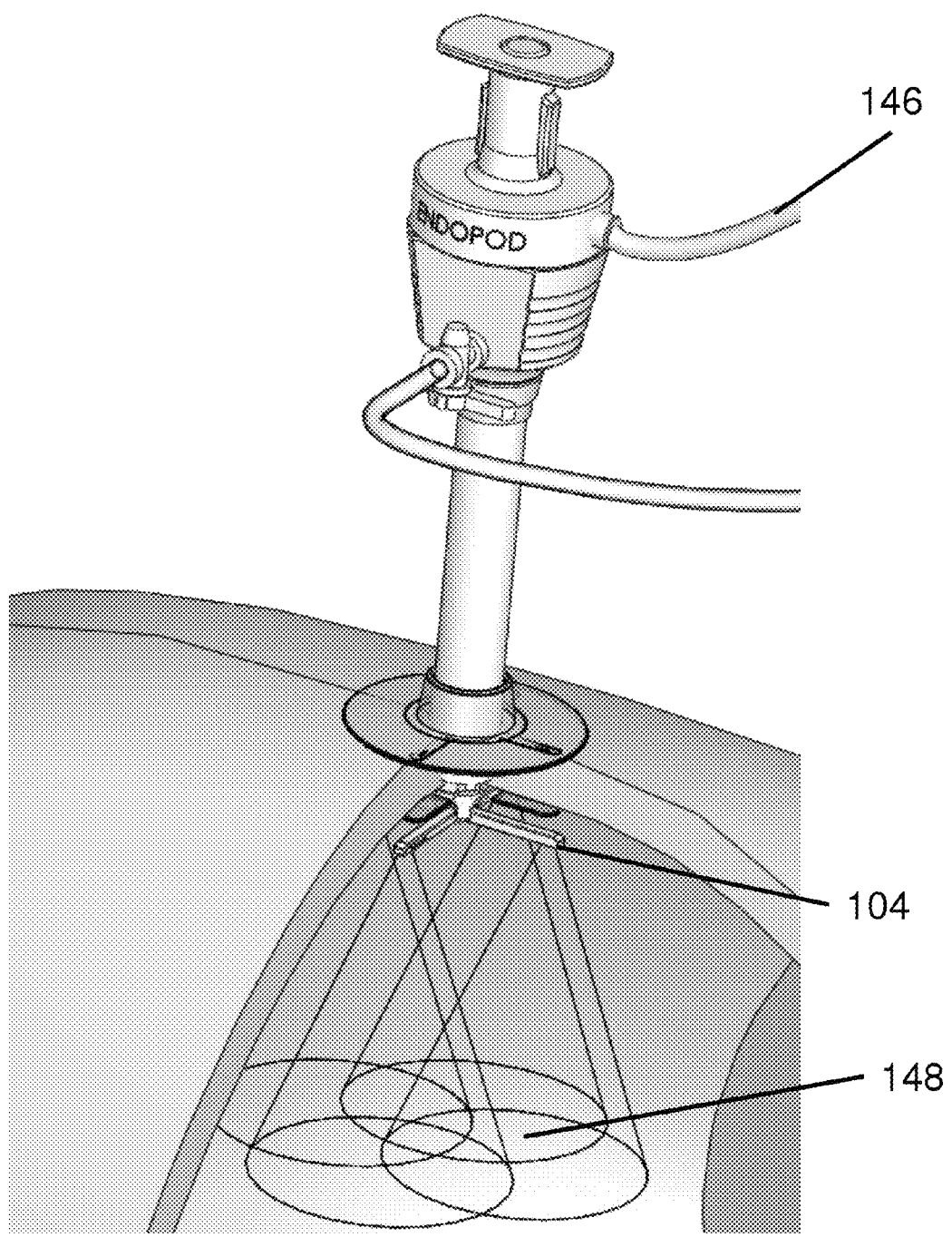
FIG. 5 illustrates a cut-away view of the abdominal wall showing the endoscope as positioned outside the body cavity and within the body cavity, and illustrating a field of view (FOV) provided by the lighting elements, optical elements and sensor elements positioned on each of the extendible arms, according to one embodiment of the invention.

FIG. 5 illustrates a field of view (FOV) 148 of the optical elements 110, such as an image sensor like a CMOS camera or a 4,000 (4K) pixel sensor, which may be positioned on one or more of the extendible arms 104. The user of numerous cameras at different positions allows for a wider field of view and provides better views of certain objects as a result of the different angles, ensuring that any area which is being examined or treated by the user can be shown at with significantly-increased clarity. The image from each of the extendible arms may be provided individually on a display or together in a segmented display all at once. In addition, the multiple viewpoints may be used to create a three-dimensional (3D) image of the interior of the body from one or more different angles of the imaging devices. The images captured by each of the imaging devices may be transmitted via the optoelectronic cable 146 to a viewer or computing device positioned on the outside end of the endoscope, where the three-dimensional image is synthesized and displayed to the user. In another embodiment, the images are sent to a separate computing device which receives and synthesizes the images into a 3D image that can then be output to a video display device, such as a monitor or television.

The FOV 148 in FIG. 5 is also illustrative of a field of view of a plurality of the lighting elements 112, such as LEDs, which may be positioned on one or more of the extendible arms 104. This arena-like lighting provides a larger surface area that can be properly illuminated and eliminate shadows by providing light from multiple angles.

Figure 6:
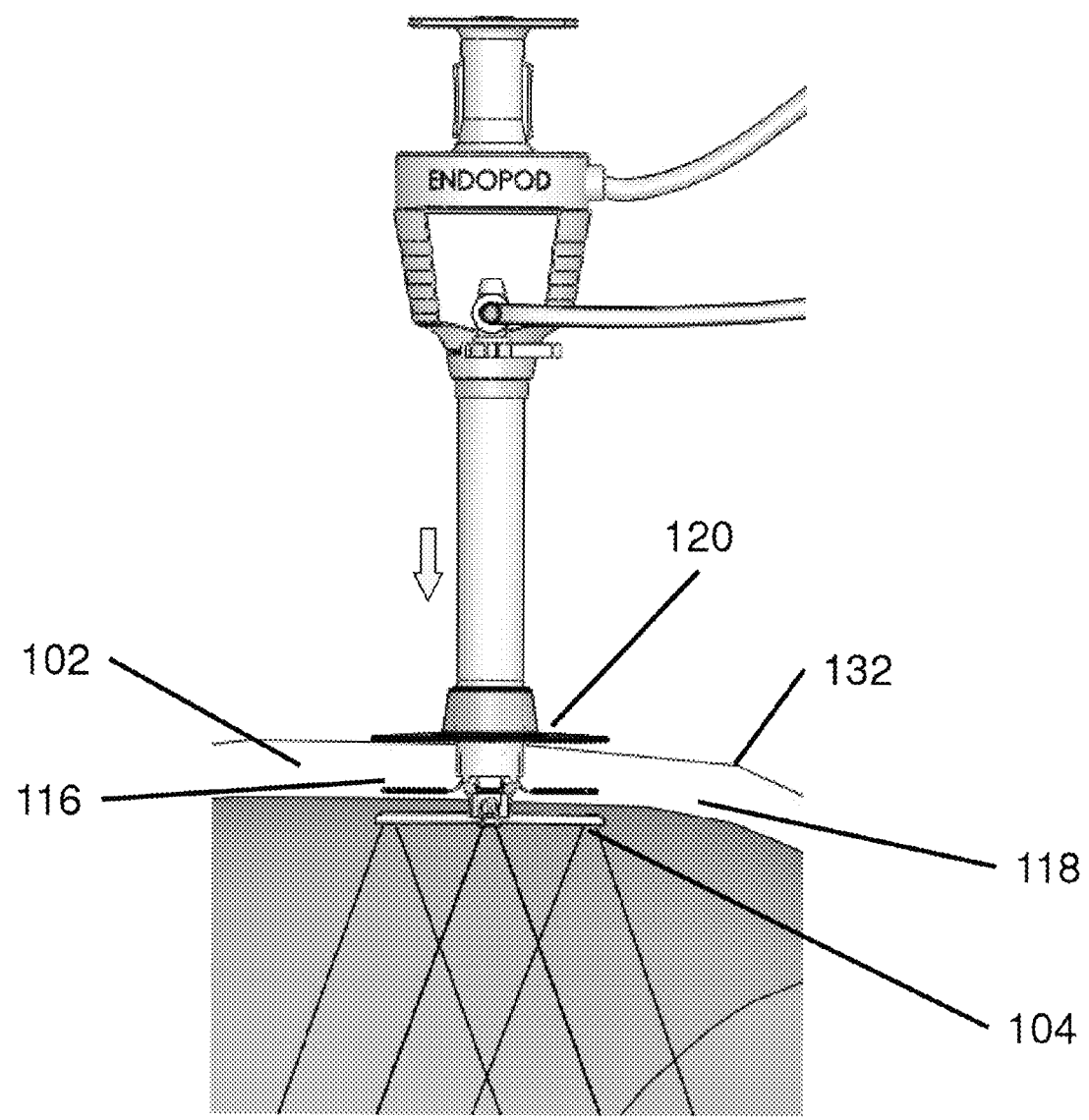
FIG. 6 is a side-view illustration of the endoscope with the support arms and stabilization plate in a locked position, according to one embodiment of the invention.

FIG. 6 illustrates the endoscope in an inserted, locked and extended configuration, with the extendible arms 104 and support arms 116 fully extended and positioned against the interior surface 118 of the abdominal wall 102. The stabilization plate 120 is also shown in its locking position in contact with the outer surface 132 of the abdominal wall. In this configuration in FIG. 6, the plurality of imaging devices may be considered locked in. The FOV 148 of each optical element or light element is also illustrated to show the overlapping coverage of the elements from each extendible arm 104.

Figures 7A, 7B, 7C:
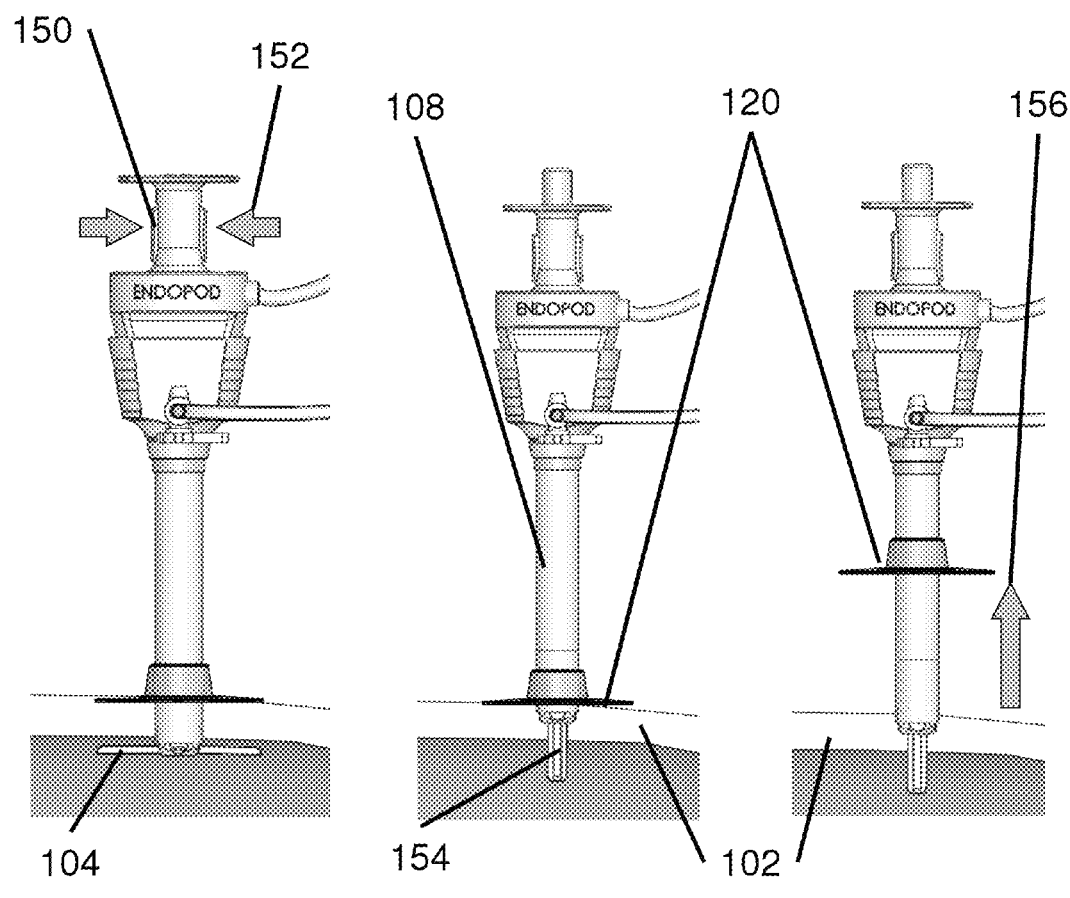
FIGS. 7A-7C are side-view illustrations of a process of activating release tabs to collapse the extendible arms and remove the endoscope from the body cavity, according to one embodiment of the invention.

FIGS. 7A-7C illustrate a process for withdrawing and removing the endoscope, which may be triggered by a mechanical switch such as the retraction tabs 150 which may be depressed as shown by the arrows 152 in FIG. 7A to unlock the extendible arms 104 (and support arms, not shown here) from their locked configuration. The extendible arms 104 and support arms 116 begin to fold back together until they are substantially parallel and in a folded configuration 154, as shown in FIG. 7B, where they can then be retracted back through the cannula 108 in the direction of arrow 156, as shown in FIG. 7C. The stabilization plate 120 is also raised away from the abdominal wall 102 so that the entire endoscope can be safely and quickly removed.

In one embodiment, a breakaway locking mechanism is provided to allow the endoscope to be manually removed if the retraction tabs 150 or other release mechanism fails. The breakaway locking mechanism is configured to allow the support arms and extendible arms to break back into the folded configuration if a sufficient amount of force is applied from the central shaft.

As mentioned above, the endoscope may be provided with less than four extendible arms, which may be configured for a particular endoscopic procedure that does not provide sufficient space for numerous extendible arms. In one embodiment, an arthroscopic endoscope is provided with a single extendible arm in order to allow the endoscope and extendible arm to fit within the space of a joint such as a knee or shoulder. For example, in an arthroscopic procedure, the view of the interior of the joint from the camera on the extendible arm provides a perspective view of the procedure which provides a surgeon with a safer mechanism for cutting that minimizes a risk of damaging the optical equipment of the extendible arm (a common occurrence in arthroscopy). Additional embodiments of the endoscope may be specially configured with different numbers of extendible arms or different lengths of extendible arms for specific purposes such as cancer treatment, colonscopy, gynological examinations and arthroscopy.

II. Endoscopic Tool with Integrated Image Capture

FIG. 8A illustrates one embodiment of an endoscopic tool 800 in the form of a stapler tool 804 with an integrated image capture device 808, according to one embodiment of the invention. The endoscopic tool 800 may be used individually or in conjunction with the multi-winged endoscope described above in order to provide additional views of an endoscopic procedure from a location immediately adjacent to the activity of the endoscopic tool. The medical instrument may be any type of endoscopic tool used during MIS, such as scissors, graspers, dissectors, staplers, etc. The interfacing end of the medical instrument may then be the portion of the medical instrument where the actual scissor blades, grasper clamps, staple arms, etc. are located.

In the embodiment illustrated and described herein, the stapler 804 contains two staple arms 810A and 810B which extend outward from a base section 818 to a point 820 where tissue will be inserted and then clamped with a staple (not shown). As shown in FIG. 8A, the image capture device 808 is integrated at the base section 818 and is pointed at the two staple arms 810A and 810B so that it captures images of the stapler being positioned over a portion of tissue to be stapled. The image capture device 808 may be disposed between the two staple arms 810A and 810B to provide an image which is as close as possible to the area immediately adjacent to the point 820 of the tool. A lighting element (not shown) may also be disposed with the image capture device 808 in order to light up a field of view (FOV) 816 of the image capture device.

The endoscopic tool 800 may also include a pivot arm 806 disposed between the base 818 of the tool 804 and a shaft 802 which connects the tool 804 with a user-operated trigger 814 on a handle 812 which is used to manipulate and actuate the tool 804. With the addition of the integrated image capture device 808, the user is then able to move the stapler 804 within a body cavity and around tissue, bone and other physiological structures into small, obscure areas while still being able to view the positioning and activity of the stapler upon actuating a trigger on the stapler device.

FIG. 8B is an illustration of the complete medical instrument illustrating the handle 812 and trigger portion 814 where a user can grasp the medical instrument and actuate the stapler 804 or other tool remotely at the interfacing end point 820. Electrical and data cables connecting the image capture device and lighting element may pass through the shaft to the handle 812 and be connected with a power source (such as a battery in the handle or a connection to an external power source) or a communication source (such as a wired or wireless communication module) to transmit the captured images to a computing and display device. In another embodiment, the image capture device may be positioned at the end point 820 of the interfacing end to provide a different viewpoint for the user, such as a medical instrument which is designed for a diagnostic-based exploratory procedure. More than one image capture device may also be integrated into various portions of the medical instrument depending on whether multiple viewpoints may be beneficial.

In one embodiment, the image capture device is an electronic image capture device such as a CMOS chip that can be easily integrated into a small tool such as the medical instrument. However, other types of image capture devices may be used, such as a camera with a built-in optical zoom in order to more clearly visualize a particular area within the body cavity. In another embodiment, the light source that is also placed near the image capture device to illuminate the area in front of the image capture device and create a properly illuminated image may be an LED or a fiber optic light source which can be easily integrated into a small medical instrument used in MIS without requiring significant power or generating significant heat.

The endoscopic tool may also be provided with one or more sensors configured to detect near infrared (near IR), fluorescence (i.e. from a dye), temperature, distance, etc.

In one embodiment, the medical instrument may be introduced into a body cavity through a cannula of an endoscope so that the endoscope and the medical instrument can share a single entry point. The image capture device on the medical instrument may be integrated with the endoscope in order to provide multiple views from inside the body cavity, including views from one or more image capture devices on the endoscope and views from the one or more image capture devices on the medical instrument.

The invention claimed is:

1. An endoscope with multifunctional extending arms, comprising:
    a central shaft with a distal end and a proximal end, and configured to be inserted through a cannula and into a body cavity;
    a plurality of extendible arms configured at the distal end of the central shaft, wherein the plurality of extendible arms extends away from the central shaft at a predetermined spatial relationship when the distal end has protruded through the cannula and into the body cavity;
    wherein the plurality of extendible arms are configured with at least one sensor element;
    a plurality of support arms extending away from the central shaft and proximal to the plurality of extendible arms, wherein the plurality of support arms are disposed against an interior surface of the body cavity wall; and
    a stabilization plate positioned around a circumference of the cannula and disposed against an exterior surface of the body cavity wall, wherein the stabilization plate includes illustrations of each extendible arm which correspond to a location of each extendible arm within the body cavity, and wherein the stabilization plate is in corresponding positional communication with the plurality of support arms such that rotational movement of the stabilization plate about the central shaft causes corresponding rotational movement of the plurality of support arms about the central shaft.

2. The endoscope of claim 1, wherein the stabilization plate includes numerical indicators on each illustration of each extendible arm corresponding to each extendible arm.

3. The endoscope of claim 1, wherein the plurality of extendible arms rotate about their length-wise axis to tilt each individual extendible arm.

4. The endoscope of claim 3, wherein the plurality of extendible arms rotate along their length-wise axis in a predetermined spatial relationship.

5. The endoscope of claim 1, wherein the stabilization plate is in locking communication with the plurality of support arms such that locking the stabilization plate into place against the exterior surface of the body cavity wall causes the plurality of support arms to lock in place against the interior surface of the body cavity.

6. The endoscope of claim 1, wherein the sensor element is an image capture device.

7. The endoscope of claim 6, wherein the extendible arm is further configured with a lighting element.

8. The endoscope of claim 7, wherein the at least one sensor element includes at least one of: an infrared sensor, a fluorescence sensor, an electrical signal sensor and a motion sensor.

9. The endoscope of claim 1, wherein the plurality of extendible arms includes two extendible arms extending in opposing directions.

10. The endoscope of claim 9, wherein the plurality of extendible arms includes four extendible arms disposed approximately 90 degrees from each adjacent extendible arm.

11. The endoscope of claim 1, further comprising a set of tabs protruding from a distal end of the cannula between each adjacent extendible arm to provide for the corresponding positional communication between the stabilization plate and the plurality of extendible arms.

* * * * *